United States Patent [19]
Field

[11] Patent Number: 5,832,920
[45] Date of Patent: Nov. 10, 1998

[54] TRACHEAL TUBE WITH INTEGRAL SUCTION LUMEN

[75] Inventor: Stephen James Field, Bridge, England

[73] Assignee: Smiths Industries Public Limited Co., London, England

[21] Appl. No.: 716,621

[22] Filed: Sep. 19, 1996

[30]     Foreign Application Priority Data

Oct. 4, 1995 [GB] United Kingdom .................... 9520234

[51] Int. Cl.⁶ ........................... A61M 16/00; A61M 1/00; A62B 9/06
[52] U.S. Cl. ............... 128/207.14; 128/205.12; 604/35
[58] Field of Search ............ 128/207.14, 207.15, 128/207.16, 911, 912, 205.12; 604/93, 96–98, 102, 118, 119, 128, 163, 171, 264, 268, 27, 35, 43, 280

[56]        References Cited

U.S. PATENT DOCUMENTS

| | | | |
|---|---|---|---|
| 3,948,273 | 4/1976 | Sanders | 128/207.15 |
| 4,508,533 | 4/1985 | Abramson | 604/35 |
| 4,607,635 | 8/1986 | Heyden | 128/207.15 |
| 4,637,389 | 1/1987 | Heyden | 128/207.15 |
| 5,188,592 | 2/1993 | Hakki | 604/35 |

*Primary Examiner*—Kimberly L. Asher
*Attorney, Agent, or Firm*—Pollock, Vande Sande & Priddy

[57]         ABSTRACT

A tracheal tube has an extruded suction lumen extending along its length on the outside of the curvature of the tube. The suction lumen opens internally to the main lumen through a series of holes, which increase in size towards the patient end of the tube. Towards the machine end of the tube, the suction lumen is connected to a suction source by which suction is applied to the suction lumen to remove secretions that collect inside the tube.

16 Claims, 2 Drawing Sheets

TRACHEAL TUBE WITH INTEGRAL SUCTION LUMEN

BACKGROUND OF THE INVENTION

This invention relates to tracheal tubes and systems.

The invention is more particularly concerned with tracheal tube suction systems and with tracheal tubes for such systems.

Tracheal tubes, such as tracheostomy or endotracheal tubes, have a patient end located in the trachea and a machine end that emerges from the patient's mouth, nose or through a surgically made opening in the neck. Tracheal tubes are used to ventilate the patient or to administer anaesthetic gases.

After a period of use, secretions build up on the inside of the tube, which can impede gas flow along the tube and provide a site for the accumulation of bacteria. In order to reduce the build-up of these secretions, it is usual periodically to suction the inside of the tube. This is done by passing a small diameter suction catheter down the bore of the tube and applying suction to the machine end of this catheter so that secretions in the region of the patient end tip of the catheter are sucked away.

One disadvantage of this is that it is difficult to direct the suctioning catheter and that suctioning may only remove secretions from a part of the tube. Another problem is that introducing the suction catheter requires the provision of a suction port in a part of the tracheal tube or in a connector coupled to the tube and that special provision has to be made if ventilation is not to be compromised by the escape of gas through this suction port. Furthermore, the introduction and removal of the suction catheter can present contamination problems both to the patient and to the clinician. It has been proposed to use closed system suction catheters in which the catheter is protected within a collapsible envelope, such as described in U.S. Pat. No. 3,991,762. These systems can be effective in preserving the sterility of the catheter before introduction and in protecting the clinician from contact with the catheter after use. However, closed system suction catheters are relatively expensive, they can be cumbersome and obscure the region of the mouth and neck, they require frequent replacement if they are not to provide a site for the accumulation of bacteria, and they present a disposal hazard after use. Previous suction arrangements also have the disadvantage that they can only be used periodically and require intervention by the clinician. Also, there is the risk that introducing the suction catheter could knock off large accumulations of secretions, which could then be conveyed deep into the lungs by the ventilation gases. This can cause infection problems.

U.S. Pat. No. 5,291,882 describes a tracheal tube with lumens extending along the wall of the tube and opening on the inside. The lumens are connected to a source of ventilation gas. U.S. Pat. No. 4,584,998 describes a multi-lumen tube with lumens used to introduce oxygen, to irrigate or to monitor gases. Tracheal tubes having lumens by which material outside the tube can be suctioned are known from, for example, U.S. Pat. No. 4,637,389, U.S. Pat. No. 4,607,635 and GB-A-2250440.

It is also possible to use a disposable inner cannula or liner that is removed and replaced periodically but this has the disadvantage of reducing the internal diameter of the gas passage through the tracheal tube. The removal and replacement of the inner cannula also usually involves some interruption to ventilation.

BRIEF SUMMARY OF THE INVENTION

It is an object of the present invention to provide an improved arrangement for the suctioning of tracheal tubes.

According to one aspect of the present invention there is provided a tracheal tube system including a tracheal tube having a main lumen extending along its length and opening at opposite ends of the tube and a minor lumen extending along a major part of the length of the tube, the minor lumen opening externally towards the machine end of the tube and opening internally into the major lumen at least at one location towards the patient end of the tube, and a suction source connected with the minor lumen where it opens externally such that secretions that collect on the inside of the tube can be removed by the suction source through the minor lumen.

The minor lumen is preferably extruded within the wall of the tube and may have a plurality of openings that open internally into the major lumen at different locations spaced along the length of the minor lumen. The size of the openings from the minor lumen into the major opening may vary along the length of the minor lumen, preferably becoming larger towards the patient end of the tube. The or each opening is preferably smaller in section than that of the minor lumen. Alternatively, the minor lumen may open internally into the major lumen through a slit extending along a part at least of the length of the minor lumen. The tracheal tube may be curved along its length, the minor lumen extending along the outer curvature of the tube. Alternatively, the minor lumen may be displaced angularly along the tube, such as by following a helical path around the tube. The minor lumen is preferably elongated in section around a part of the circumference of the tube. The suction source preferably includes a suction vessel for containing aspirated material, the suction vessel having an inlet connected with said minor lumen, and a pump connected with an upper end of the vessel to pump out air from the vessel thereby creating suction at the inlet. The suction source preferably automatically applies suction periodically to the minor lumen and may be arranged to apply suction either only during inhalation or only during exhalation.

According to another aspect of the present invention there is provided a tracheal tube for a system according to the above one aspect of the invention.

A tracheal suction tube and system, in accordance with the present invention, will now be described, by way of example, with reference to the accompanying drawings.

DETAILED DESCRIPTION OF THE PREFERRED EMBODIMENTS

Figure 1:
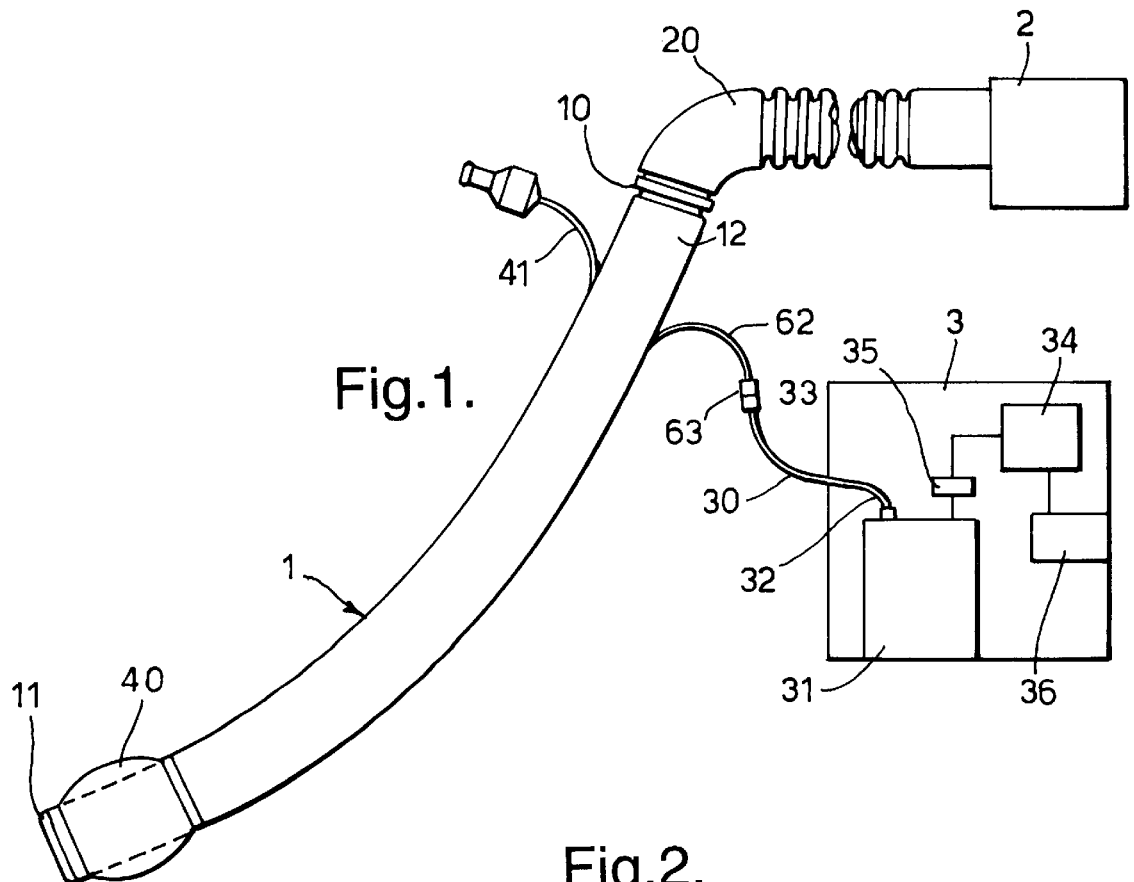
FIG. 1 shows the system schematically.

The system shown in FIG. 1 comprises an endotracheal tube 1, a ventilating machine 2, a breathing circuit 20, a connector 10 connecting the ventilating machine to the tube, a suction source 3 and suction tubing 30 connecting the suction source to the endotracheal tube.

Figure 2:
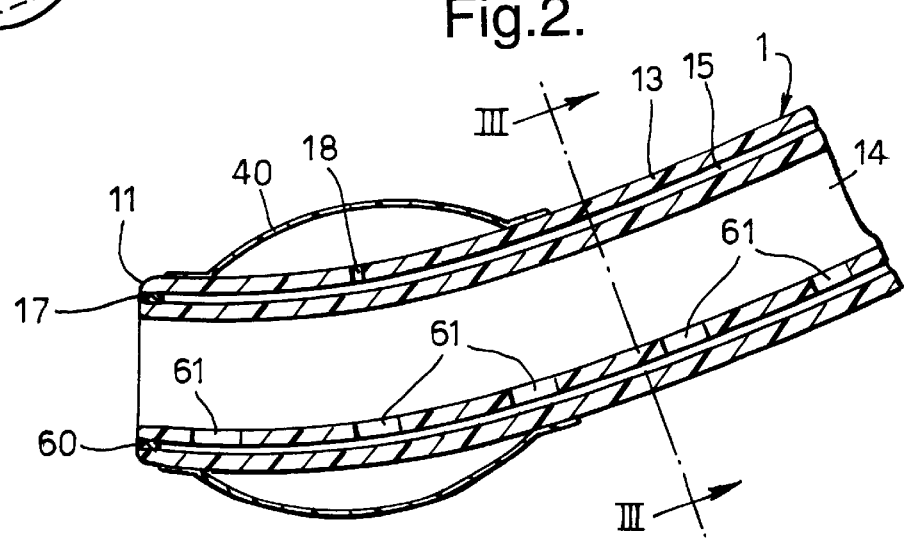
FIG. 2 is a sectional side elevation of a part of the tube to an enlarged scale.
Figure 3:
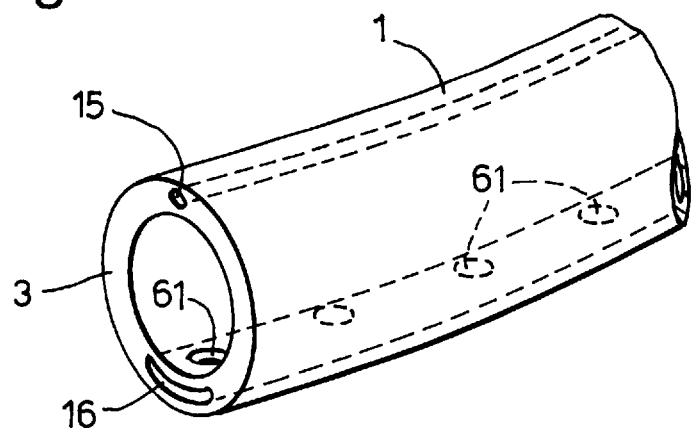
FIG. 3 is a cutaway perspective view of the tube along the line III—III of FIG. 2.

With reference now also to FIGS. 2 and 3, the endotracheal tube 1 has a patient end 11, which, in use, is located in the trachea of the patient. The tube 1 has a smooth outer surface and is curved along its length to follow the curvature of the trachea, with the machine end 12 of the tube projecting from the mouth of the patient (not shown). The tube has a wall 13 of circular section extruded from PVC, or a similar plastics material, with three lumens 14, 15 and 16. The main lumen 14 is of circular shape and extends axially along the entire length of the tube 1 from its patient end 11, where it opens externally of the tube, to its machine end 12, where it opens into the connector 10. The cross-sectional area of the main lumen 14 extends across the major part of the cross sectional area of the tube 1 as a whole. The lumen 14 is used to convey breathing gases to and from the trachea and hence to the respiratory system of the patient.

One of the minor lumens 15 is of circular section and extends within the wall 13 of the tube along its entire length, although it is sealed closed by a plug 17 at the patient end 11 and by a similar plug (not shown) at the machine end. Alternatively, the lumen 15 could be closed at its ends by welding. The minor lumen 15 opens through a small aperture 18 through the exterior of the wall 13 into a cuff 40. The cuff 40 extends around the tube 1 close to its patient end and, when inflated, seals the tube to the inside of the trachea so that gas flow is confined along the main lumen 14 of the tube. The minor lumen 15 is used for inflation and deflation of the cuff 40 and communicates with a cuff inflation line 41 via an opening made into the lumen from the outside of the tube towards its machine end 12.

The second minor lumen 16 is a suction lumen and is used to remove secretions from the inside of the tube 1. The suction lumen 16 extends within the thickness of the wall 13 and is located diametrically opposite the cuff-inflation lumen 15, on the outside of the curvature of the tube. Generally, in use, the patient is laid on his back and the outside of the curvature of the endotracheal tube 1 is located downwardly so the suction lumen 16 is located along the lower side of the tube. The suction lumen 16 extends along the entire length of the tube 1 but is closed at the patient end 11 by a plug 60 or by welding; the lumen is similarly closed by a plug (not shown) at the machine end 12 of the tube. The suction lumen 16 is elongated in section around a part of the circumference of the tube to form a crescent-shape having a cross-sectional area greater than that of the cuff-inflation lumen 15, so as to allow for the free flow of secretions and mucus along the lumen. The suction lumen 16 opens into the interior of the tube, that is, the major lumen 14, through a series of circular apertures 61 formed on the interior of the wall 13 breaking through to the suction lumen. The first aperture is located adjacent the patient end 11 of the tube and the other apertures are spaced equally along the length of the tube. Typically, the apertures 61 may be spaced from one another by a distance of about 2 cm with about 15 apertures in all; however, the number of apertures may vary from one to as many as about 50. The apertures could be spaced irregularly, such as, for example, to give a greater suctioning towards the patient end of the tube or to accommodate for loss of suction pressure along the length of the tube. In the present example, the aperture 61 closest to the patient end 11 of the tube 1, has the largest diameter and the other apertures reduce in size towards the machine end 12 of the tube. This compensates for the reduction in suctioning pressure towards the patient end of the tube so that an equal suctioning effect is produced at each aperture. The cross sectional area of the largest of the apertures 61 is preferably smaller than that of the suction lumen 16 so as to reduce the risk of blockage in the suction lumen. At a point close to the machine end 12 of the tube 1, a suction line 62 is joined to the suction lumen 16 via an opening cut into the outside of the wall 13. Alternatively, the suction line 62 could be connected to the suction lumen 16 by means of a collar joined to the machine end of the tube 1. The machine end of the suction line 62 is terminated by a connector 63, which is in turn joined to a connector at the patient end of the suction tubing 30. The suction tubing 30 extends to the suction source 3.

The suction source 3 comprises a collection vessel 31, such as a bottle, having an inlet 32 at its upper end connected to the suction tubing 30. An outlet 33 of the bottle 31, also at its upper end, connects to a vacuum pump 34 via a conventional filter 35. The suction source 3 also includes a control unit 36 by which operation of the pump 34, and hence the source itself, is controlled. The control unit 36 automatically turns on the pump 34 for short intervals periodically. Alternatively, the control unit 36 may be arranged to maintain the pump on continuously during intubation or it may be controlled manually to turn the pump on only when desired by the clinician. The pump could be arranged to apply suction only during inhalation or only during exhalation, if desired. Various alternative suction systems are possible. For example, the pump could be provided by a venturi system arranged to create a negative, suctioning pressure at the machine end of the suction tubing 30. The venturi system could be driven by any convenient source of pressurized gas, such as a compressor or other air supply, such as the ventilator itself.

In use, the cuff 40 is inflated to seal the outside of the tube 1 with the trachea of the patient, and the ventilating machine 2 supplies ventilation or anaesthetic gases along the main lumen 14 of the tube. When the pump 34 is operated, it applies a reduced pressure to the outlet 33 of the collection vessel 31 causing suction to be applied to the inlet 32 of the vessel and hence to the suction tube 30. This in turn applies suction to the suction line 62 and to the suction lumen 16. Any secretions and mucus entering the tube 1 will tend to collect inside the outer part of the curvature of the tube because this lies lower than the inner part of the curvature. The secretions will also tend to move along the tube 1 under the action of gravity and the flow of ventilation gases. As this happens, the secretions will move to one or other of the suction apertures 61 where they will be aspirated into the suction lumen 16 and to the suction source 3.

The arrangement of the present invention has the advantage that suctioning can take place without the need to interrupt ventilation. It avoids the need to use a connector with a suction port through which a suction catheter is inserted. By avoiding the need to use a suction catheter, there is less risk of contamination to the patient and the clinician, and there is less wastage and hazard from contaminated articles. The invention also has the advantage that suctioning can be achieved automatically or continuously and without the need for intervention by the clinician.

Figure 4:
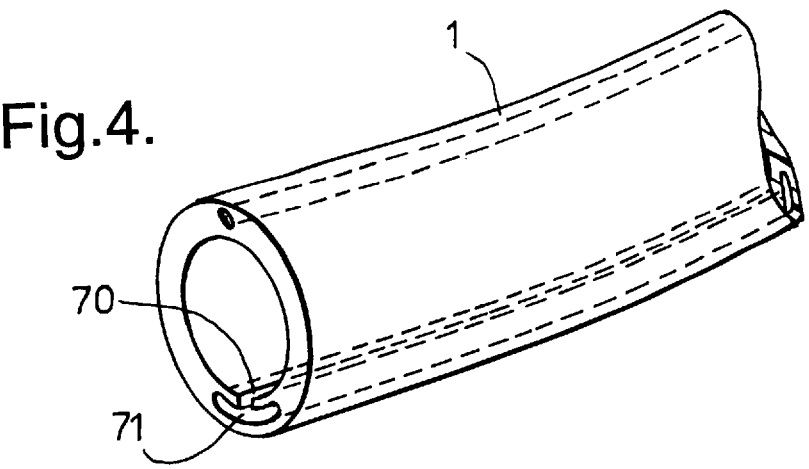
FIG. 4 is a cutaway perspective view of an alternative tube.

Various alternative forms of tube are possible. For example, as shown in FIG. 4, a small slit 70 extends along the length, or along a part of the length of the suction lumen 71. The slit 70 is narrow enough to ensure that there is sufficient vacuum pressure at the patient end of the tube to produce effective suctioning but is still wide enough to allow passage of secretions into the suction lumen 71.

Figure 5:
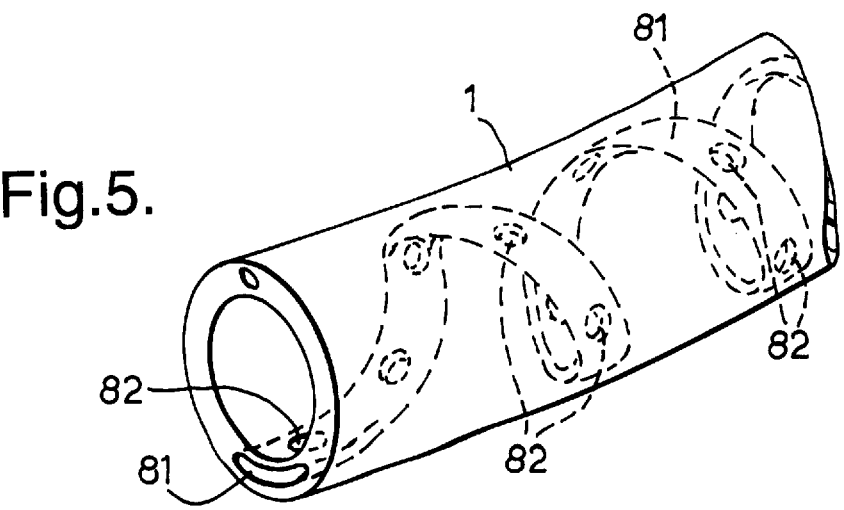
FIG. 5 is a cutaway perspective view of another tube.

In another arrangement, as shown in FIG. 5, the suction lumen 81 takes a helical path so that the suction apertures 82 are located at different points around the circumference of the tube. This arrangement can be advantageous where the tube is used in a more vertical orientation and where there is less tendency for the secretions to collect in one part of the tube. The helical lumen can be produced during the extrusion process by twisting the tubing as it emerges from the extruder. The suction lumen could be angularly displaced about the axis of the tube along its length in other fashions, such as by following a wavy track along the length of the tube.

What I claim is:

1. A tracheal tube system comprising a tracheal tube, said tube having a main lumen extending along its length and opening at opposite ends of said tube and a minor lumen integral with a wall of said tube and extending with said wall along a major part of the length of said tube, said minor lumen opening externally towards a machine end of said tube and opening internally into said major lumen at least at one location towards a patient end of said tube;

a suction source; and a connection between said suction source and said minor lumen where it opens externally such that secretions that collect on the inside of said tube can be removed by said suction source through said minor lumen.

2. A system according to claim 1, wherein said minor lumen is extruded within said wall of said tube.

3. A system according to claim 1, wherein said minor lumen has a plurality of openings that open internally into said major lumen at different locations spaced along the length of said minor lumen.

4. A system according to claim 3, wherein the size of said openings from said minor lumen into said major lumen vary along the length of said minor lumen.

5. A system according to claim 4, wherein said openings are larger towards the patient end of said tube.

6. A system according to claim 1, wherein the or each said opening from said minor lumen into said major lumen is smaller in section than that of said minor lumen.

7. A system according to claim 1, wherein said minor lumen opens internally into said major lumen through a slit extending along a part at least of the length of said minor lumen.

8. A system according to claim 1, wherein said tracheal tube is curved along its length, and wherein said minor lumen extends along the outer curvature of said tube.

9. A system according to any one of claim 1, wherein said minor lumen is displaced angularly about the length of said tube.

10. A system according to claim 9, wherein said minor lumen follows a helical path around said tube.

11. A system according to claim 1, wherein said minor lumen is elongated in section around a part of the circumference of said tube.

12. A system according to claim 1, wherein said suction source includes a suction vessel for containing aspirated material, said suction vessel having an inlet connected with said minor lumen, and a pump connected with an upper end of said vessel to pump out air from said vessel thereby creating suction at said inlet.

13. A system according to claim 1, wherein said suction source automatically applies suction periodically to said minor lumen.

14. A system according to claim 1, wherein said suction source is arranged to apply suction either only during inhalation or only during exhalation.

15. A tracheal tube system comprising a tracheal tube, said tube being curved along its length and having a main lumen and a minor lumen extending within a wall of said tube along a major part of the length of said tube along an outer curvature of said tube, said minor lumen opening externally towards a machine end of said tube and opening internally into said major lumen at a plurality of locations along the length of said tube;

a suction source; and a connection between said suction source and said minor lumen where it opens externally such that secretions that collect on the inside of said tube can be removed by said suction source through said minor lumen.

16. A tracheal tube comprising a wall;

a main lumen extending along the length of the tube and opening at both ends of the tube;

a suction lumen extending along a major part of the length of the tube within said wall;

a plurality of openings in said wall, said openings opening from said suction lumen to said main lumen; and a suction line joined with said suction lumen towards a machine end of the tube such that secretions that collect on the inside of said wall of said tube can be removed via said openings and said suction lumen by applying suction to said suction line.

* * * * *